United States Patent [19]

Fletcher et al.

[11] 4,018,080
[45] Apr. 19, 1977

[54] DEVICE FOR TENSIONING TEST SPECIMENS WITHIN AN HERMETICALLY SEALED CHAMBER

[76] Inventors: James C. Fletcher, Administrator of the National Aeronautics & Space Administration, with respect to an invention of; Page K. Evans, Athens; Dan L. Shady, Huntsville, both of Ala.

[22] Filed: Feb. 13, 1976

[21] Appl. No.: 657,995

[52] U.S. Cl. .................................. 73/15.6; 73/95
[51] Int. Cl.² ......................................... G01N 3/18
[58] Field of Search ............................ 73/156, 95

[56] References Cited

UNITED STATES PATENTS

| | | | |
|---|---|---|---|
| 2,436,317 | 2/1948 | Manjoine | 73/15.6 |
| 3,176,499 | 4/1965 | Sikora | 73/15.6 |
| 3,404,562 | 10/1968 | MacGlashanje et al. | 73/15.6 |
| 3,491,586 | 1/1970 | Branger | 73/15.6 X |
| 3,922,903 | 12/1975 | Bornstein et al. | 73/15.6 |

FOREIGN PATENTS OR APPLICATIONS 1,316,591 12/1962 France ................................. 73/15

OTHER PUBLICATIONS

Reed, "A Cryostat For Tensile Tests in the Temperature Range of 300°–4° K", in Crygenic Materials Data Handbook, Sept., 1961.

Erdmann, "Apparatus For Low-Temperature Deformation and Simultaneous Measurements of Thermal Properties of Metal", in Rev. of Sci. Inst. vol. 34, No. 2, Feb., 1963, pp. 172–179.

Vergola et al., "A Machine For Studying Deformation At Temperatures Down To 1°–5° K", in Cryogenics, vol. 11, No. 2, Apr., 1971, pp. 148, 149.

Primary Examiner—Herbert Goldstein
Attorney, Agent, or Firm—L. D. Wofford, Jr.; George J. Porter; John R. Manning

[57] ABSTRACT

A device for tensioning test specimens within an hermetically sealed chamber. The device is characterized by a support column adapted to be received within an insulated, hermetically sealable chamber, a plurality of anchor pins mounted on the column for releasibly connecting thereto a plurality of test specimens, a plurality of axially displaceable pull rods received by the column in coaxial alignment with the anchor pins, one end of each pull rod being provided with a coupling for connecting the pull rod to a test specimen, while the opposite end of the pull rod is extended through a cover plate and adapted to be connected with a remotely related linear actuator through a connecting link including a load cell for measuring stress as the pull rod is placed in tension by the actuator.

1 Claim, 10 Drawing Figures

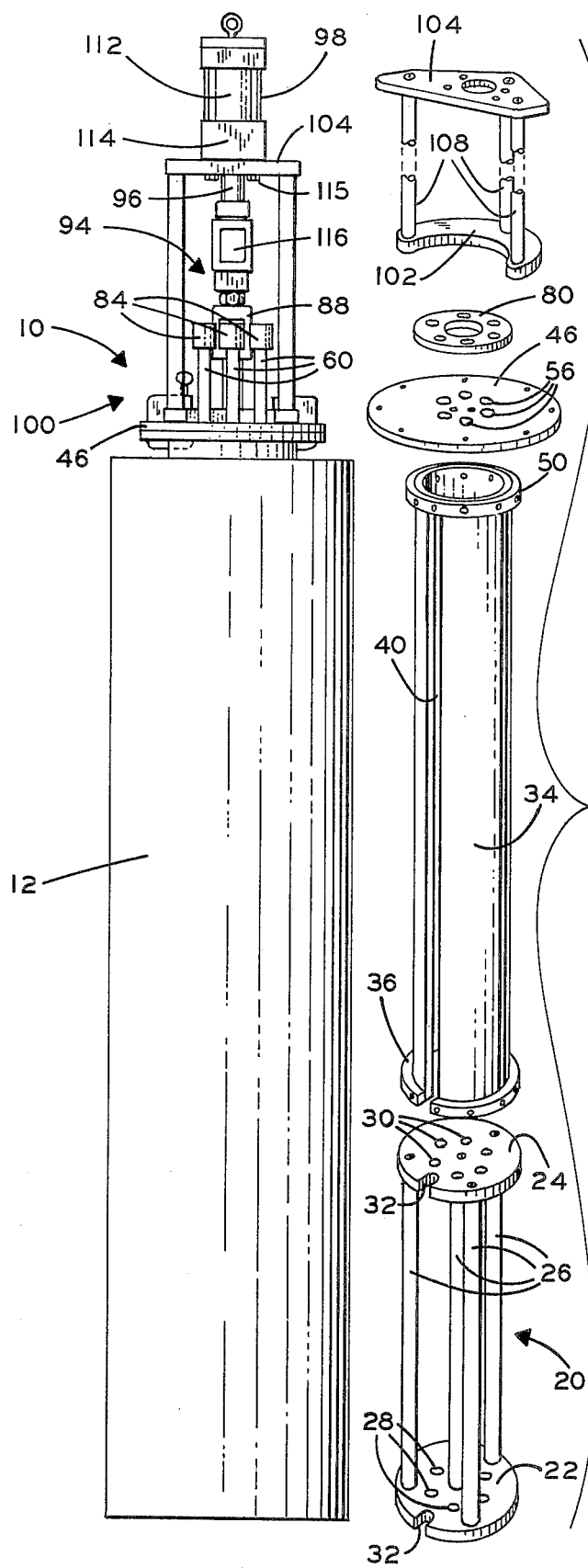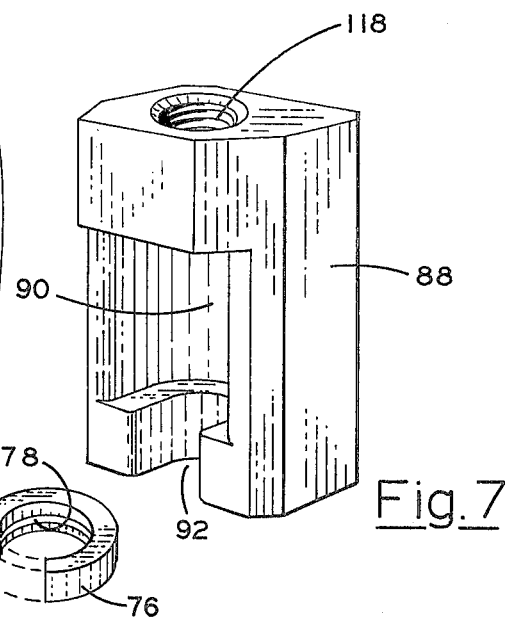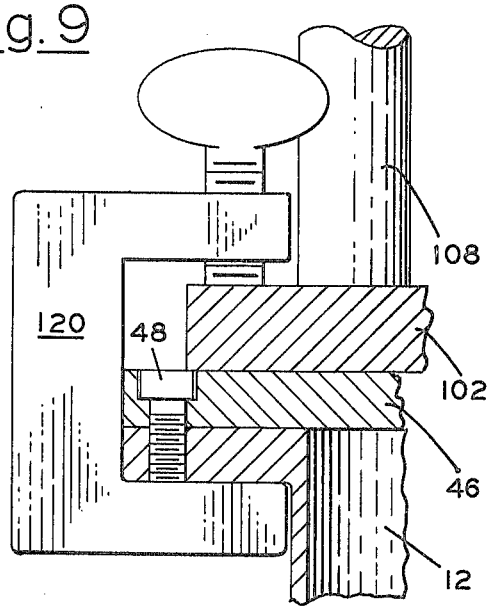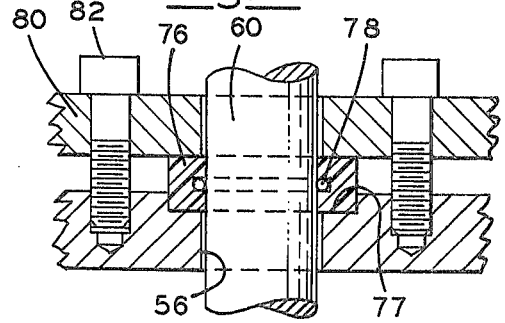

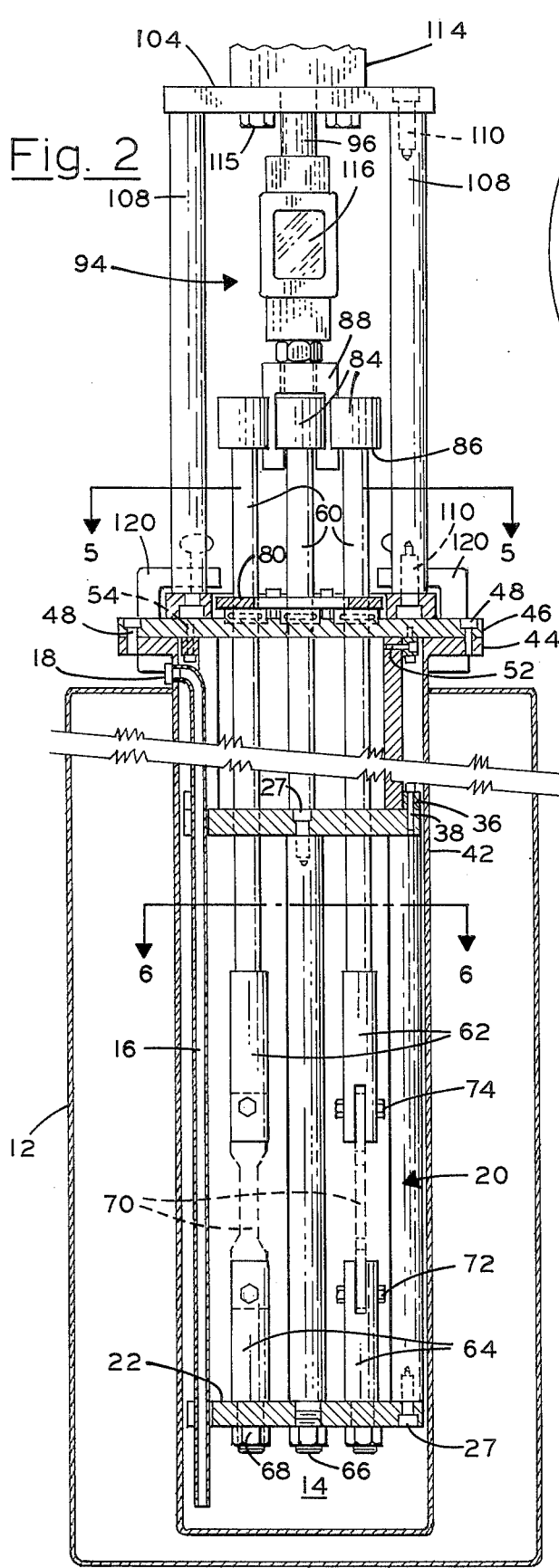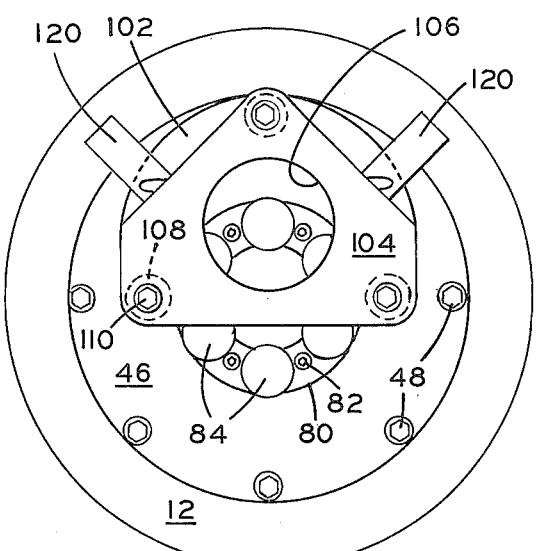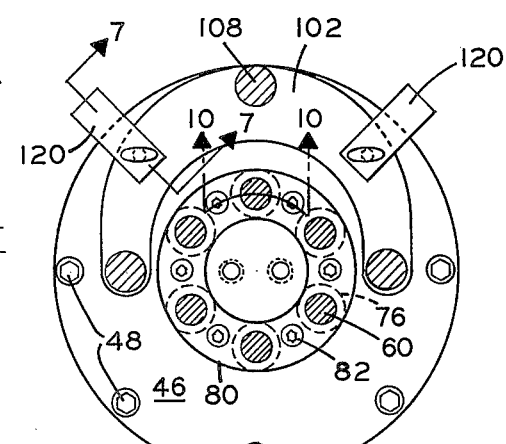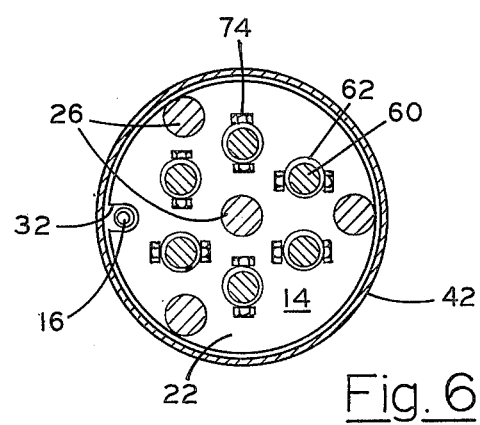

DEVICE FOR TENSIONING TEST SPECIMENS WITHIN AN HERMETICALLY SEALED CHAMBER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention generally relates to devices for tensioning test specimens, and more particularly to a device for tensioning often referred to in art simply as "pulling", test specimens within an hermetically sealed chamber defined in a dewar, whereby effects of tensile stress induced in test specimens at cryogenic temperatures can be observed.

With the advent of the design and fabrication of vehicles for space travel a great deal of attention has been given to characteristics of materials at cryogenic temperatures, as found in a celestial space environment. Not only has it been deemed necessary to determine the effects of low temperature on metals, it often is necessary, or at least desirable, to determine the effects of low temperatures on other materials such as epoxy resins and the like.

2. Description of the Prior Art

It is, of course, appreciated that commercially available devices have been employed for purposes of subjecting test specimens to the effects of tensile stress in low temperature environments. However, such devices often are designed to perform a specific testing function and, therefore, tend to be expensive, complex and often impractical to employ in testing procedures of a general nature.

Consequently, there exists a need for a device having a capability of serially tensioning a plurality of test specimens in a cryogenic environment, such as a liquid hydrogen bath, and adapted to be received in dewars of conventional design, without requiring the dewars to be extensively modified.

It is, therefore, the general purpose of the instant invention to provide a device having a capability for being received within a dewar of a conventional design and employed in serially tensioning a plurality of test specimens supported in a liquid hydrogen bath, without requiring a modification of the dewar to impart thereto a capability for withstanding tensile stress of the magnitude to which the test specimens are to be subjected.

OBJECTS AND SUMMARY OF THE INVENTION

It is, therefore, an object of the instant invention to provide a device for tensioning test specimens within a dewar of a known design.

It is another object to provide in combination with a dewar of a known design a device for tensioning test specimens.

It is another object to provide a device for tensioning test specimens within commercially available dewars for subjecting a plurality of test specimens to tensile forces of magnitudes greater than 10,000 pounds.

It is another object to provide a device for serially tensioning a plurality of test specimens within a dewar, without subjecting the dewar to tensile stress.

Another object is to provide a device for tensioning test specimens which is particularly useful in observing the effects of stress in specimens subjected to tensile stress although not necessarily restricted in use thereto since the device may be used for observing the effects of low temperatures on adhesive employed in mounting strain gauges and the like on test specimens.

These and other objects and advantages are achieved through the use of a device including a support column adapted to be placed in compression and configured to be received within an existing dewar, anchor pins for releasibly coupling a plurality of test specimens within the column, each having one end rigidly affixed to one end of the column and one end releasibly connected to a test specimen, a plurality of pull rods, each being extended into the chamber and connected with a specimen, and an actuator adapted to be connected with each of the pull rods, through a link including a load cell, for serially placing the pull rods in tension for thereby subjecting the test specimens to stress loading as the column acts in compression for dissipating the force applied by the actuator to each test specimen.

BRIEF DESCRIPTION OF THE DRAWINGS

FIG. 1 is an elevational view of the device for tensioning test specimens which embodies the principles of the instant invention including a dewar having mounted thereon a linear actuator connected with one of a plurality of projected pull rods through a connecting link including a load cell.

FIG. 2 is a fragmented, vertically sectioned view of the device shown in FIG. 1.

FIG. 3 is an exploded perspective view illustrating a support column, spacer, cover plate, retainer ring, and actuator support, employed by the device.

FIG. 4 is a top plan view of the device with the actuator removed for the sake of clarity.

FIG. 5 is a horizontally sectioned plan view taken generally along line 5—5 of FIG. 2.

FIG. 6 is a horizontally sectioned plan view taken generally along line 6—6 of FIG. 2.

FIG. 7 is a perspective view on an enlarged scale, of a female coupling provided for connecting the actuator with a pull rod.

FIG. 8 is an enlarged fragmented view depicting a C-clamp provided for coupling the actuator support with the cover plate shown in FIGS. 2 and 3.

FIG. 9 is an enlarged fragmented cross-sectional view illustrating a seal provided for providing an hermetic seal between a pull rod and a cover plate for the dewar.

FIG. 10 is a cross-sectional view illustrating the seal of FIG. 9 secured in an operative relationship with a pull rod.

DESCRIPTION OF THE PREFERRED EMBODIMENT

Referring now to the drawings, wherein like reference characters designate like or corresponding parts throughout the several views, there is shown in FIG. 1 a device, generally designated 10, which embodies the principles of the instant invention.

It is to be understood that the device 10 is particularly suited for use with a commercially available dewar, designated 12. Since the dewar 12 forms no specific part of the instant invention, a detailed description thereof is omitted. However, it is to be understood that within the dewar 12 there is a chamber 14 suitably configured for receiving and confining cryogenic fluids, such as liquid hydrogen and the like, introduced through a filler tube 16 having a suitable closure valve 18 located at the entrance thereto.

As best shown in FIGS. 2 and 3, the device of the instant invention includes a support column, generally designated 20. The column 20 is designed to act in compression and includes a base plate 22, a top plate 24, and a plurality of parallel compression bars 26 extended between the top and bottom plates for supporting the base plate and top plate in mutually spaced relation, as a compression load is imposed on the column. The plates 22 and 24 are connected with the compression bars 26 through suitable screws 27 extended through the plates and received in internally threaded bores formed in the compression bars, as best illustrated in FIG. 2. The base plate 22 includes an annular array of bores 28, while the top plate 24 includes an annular array of bores 30 arranged in coaxial alignment with the bores 28. Additionally, the plates 22 and 24 each includes a relief 32 which serves to accommodate passage of a filler tube 16 as the support column is axially inserted into the chamber 14.

A spacer 34 of a cylindrical configuration is provided for supporting the column 20 in place within the dewar. The spacer 34 includes an annular lip 36 disposed in juxtaposition with the top plate 24 of the support column and is connected thereto through a plurality of suitable screws 38. Thus, through these screws the spacer 34 and the support column 20 are integrated into a single cylindrical unit. It is important to note that the spacer 34 includes an elongated slot 40, FIG. 3, arranged in coaxial alignment with the reliefs 32, also for the purposes of accommodating passage of the filler tube 16 as the support column and spacer are inserted into the chamber 14 in an integrated relationship.

As best illustrated in FIG. 2, the chamber 14 is defined, in part, by a cylindrical wall 42 which terminates in an annular shoulder 44. This shoulder serves to receive a cover plate 46 provided for closing the uppermost end of the chamber 14, whereby an hermetic seal is established for the chamber. The cover plate 46 is secured to the shoulder 44 by a plurality of uniformly spaced screws 48 received in internally threaded openings, not designated.

In order to secure the support column 20 and spacer 34 within the chamber 14, an annular collar 50, FIG. 3, is provided in circumscribing relation with the uppermost end of the spacer 34. The collar is secured to the spacer by a plurality of screws 52, FIG. 2. The collar 50, in turn, is fastened in coaxial relation to the cover plate 46 through a plurality of uniformly spaced screws 54 extended through the collar and received in internally threaded bores, not designated, formed in the cover plate 46.

The cover plate 46 is provided with an annular array of bores 56 arranged in coaxial alignment with the bores 28 and 30. The bores 30 and 56 serve to receive an annular array of pull rods 60 which are extended therethrough in mutual parallelism as the pull rods are inserted into the column 20.

Subsequent to the pull rods 60 being inserted into the column couplings 62 are connected at the innermost ends thereof. The couplings 62, where desired, are connected with the pull rods 60 through a use of mated threads, not shown, which establish a union therebetween. The coupling 62, facilitates a connection of the pull rods 60 with test specimens in a manner which will hereinafter become more readily apparent.

Seated in the bores 28 of the base plate 22, there is a plurality of anchor pins 64. As a practical matter, the anchor pins 64 include a screw threaded portion 66 extended through the plate 22 for receiving nuts 68. These nuts serve to secure the anchor pins 64 in place.

As shown in FIG. 2, the anchor pins 64 are connected to test specimens 70 employing pins 72. These pins, where so desired, comprise screw-threaded pins extended through coaxially aligned bores formed in the anchor pins 64 and test specimen 70. Suitable nuts, not designated, are provided for securing the pins in place. Similarly, the couplings 62 are united with the test specimens 70 employing pins 74 extended through coaxially aligned openings formed in the couplings 62 and the specimens 70.

An hermetic seal is established between the pull rods 60 and the cover plate 46 by Teflon seals 76, seated in annular receptacles 77, including internal O-rings 78, FIG. 9. The O-rings 78 are seated in annular grooves suitably formed within the Teflon seals 76 in circumscribing relation with the pull rods 60, as best illustrated in FIG. 10.

Each of the seals 76 is supported in place by an annular retainer plate 80 affixed to the cover plate 46 through a plurality of screws 82 seated in suitably formed openings and received in internally threaded bores, not designated, formed in the cover plate 46.

At the extended external end of each of the pull rods 60, there is provided a protuberance 84 which functions as a coupling head. The coupling head is of a substantially cylindrical configuration and includes an annular shoulder 86 through which the coupling head can be mated with a female coupling 88.

The female coupling 88 includes a chamber 90 having an internal diameter substantially equal to the external diameter of the coupling head, formed by the protuberance 84, and a throat 92 having a cross-sectional dimension substantially equal to the external diameter of one of the pull rods 60. The length of the chamber 90 and the height of the coupling head are suitably dimensioned so that the coupling head is readily received within the chamber of the female coupling 88.

The female coupling 88 is connected at the lowermost end of a connecting link, generally designated 94, FIG. 2. The connecting link 94 is, in turn, affixed to the distal end of an axially displaceable shaft 96 provided for a linear actuator, generally designated 98, FIG. 1.

The actuator 98 is mounted on an actuator support, generally designated 100, which includes a base plate 102, of a substantially U-shaped configuration, and a top plate 104. The top plate is provided with an opening 106, coaxially aligned with the opening of the base plate, through which the shaft 96 is extended. The base plate and top plate of the actuator support 100 are interconnected by a plurality of uniformly spaced compression bars 108 arranged in parallelism. The bars 108 are rigidly united with the base and top plates 102 and 104 through a plurality of suitable screws 110 extended through the plates and received within internally threaded bores, not designated.

The actuator 98 includes a double-acting hydraulic cylinder 112, of a suitable design, adapted to be connected with a pressurized source of hydraulic fluid, not shown, and supported by a base 114 connected to the top plate 104 by suitable screws 115.

In view of the foregoing, it should be apparent that by selectively pressurizing the hydraulic cylinder 112, the shaft 96 is retracted relative to the cylinder for thus retracting the connecting link 94. Such retraction serves to induce tensile stress in the link when the link in connected with a pull rod 60 through the coupling 88. In order to measure tensile stress thus developed within the link 94 there is provided a load cell 116, of any suitable design, operatively connected to the link 94. Since the load cells are well known and the load cell 116 forms no specific part of the instant invention, a detailed description thereof is omitted in the interest of brevity. However, as should be appreciated by those familiar with such devices, as stress is developed within the connecting link 94 the stress is transmitted to the load cell while an electrical output signal is derived from the load cell 116 which comprises intelligence indicative of the stress developed in the connecting link.

Moreover, the particular manner in which the female coupling 88 is joined to the connecting link 94 and the manner in which the connecting link 94 is joined to the shaft 96 is a matter of convenience only. As a practical matter, externally threaded shafts received with internally threaded bores, typified by the bore 118, FIG. 7, function quite satisfactorily for this purpose. It is to be understood that the actuator support 100 is, in operation, repositioned to different locations relative to the cover plate 46 and the array of pull rods 60 in order to facilitate a connection of the coupling 88 with all of the pull rods 60. Such repositioning of the actuator support 100 is accommodated through the use of a pair of manually operable C-clamps 120 which when manipulated releasibly couple the actuator support to the shoulder 44.

It is important, also, to note that the device of the instant invention is assembled without the use of welds in view of the cryogenic temperatures encountered during testing operations.

OPERATION

It is believed that in view of the foregoing description, the operation of the device will readily be understood and it will be briefly reviewed at this point.

The device of the instant invention is prepared for operation by connecting the support column 20 and the spacer 34 into an integrated relationship and then connect therewith the cover plate 46, employing the screws 48. The anchor pins 64 are secured to the base plate 22, employing the nut 68, while the pull rods 60 are axially inserted through the coaxially aligned bores 56 and 30. The couplings 62 are connected to the pull rods 60 following insertion of the pull rods through the bores 56 and 30. Between the couplings 62 and the anchor pins 64 there are extended specimens 70 to be stressed. The specimens are secured to the anchor pins and couplings 62 employing the pins 72 and 74 extended through the specimens and secured in place, as illustrated in FIG. 2.

The thus assembled support column, spacer, cover plate, anchor pins, pull rods, and specimens 70 are axially inserted into the chamber 14 of the dewar 12, passage of the filler tube 16 being accommodated by the reliefs 32 and slot 40 of the support column and spacer, respectively. The cover plate is secured in place employing screws 48. Thus the dewar is substantially sealed. A cryogenic liquid, such as liquid hydrogen, subsequent to suitable flushing of the chamber 14, is introduced into the chamber via the closure valve 18. The actuator support 100, having the actuator 98 mounted thereon, is seated in an operative position on the cover plate 46. As the actuator support is seated, the female coupling 88 receives the coupling head, formed by a protuberance 84 of a given pull rod 60, in a mated relationship. Of course, repositioning of the actuator support is continued until such time as the connecting link 94 assumes a coaxial relationship with the pull rod. The actuator support is now secured in place through a manipulation of the C-clamps 120. Thus the device is prepared for a cycle of operation.

A cycle of operation for the device 10 is initiated by selectively energizing the hydraulic cylinder 112 suitably for retracting the shaft 96, thus the pull rod 60 attached to the connecting link 96 through the coupling 88 is placed in tension. Tensioning of the pull rod, of course, serves to induce stress to the specimen 70 disposed between the coupling 62 attached to the pull rod 60 and the coaxially aligned anchor pin 64 affixed to the support column 20 and spacer 34. Tensioning of the pull rod 60 places the support column 20 in compression without transmitting stress to the dewar 12. The stress thus induced in the specimen is indicated by the signal derived from the load cell 116.

Once stressing of the specimen has been completed, the hydraulic cylinder 112 is reversely pressurized for relaxing the actuator 98, by extending the shaft 96, whereupon the tensile load is removed from the pull rod 60. The C-clamps 120 are released, and the actuator support repositioned for again mating the coupling 88 with a protuberance forming a coupling head for a pull rod, in the manner hereinbefore described. The C-clamps are again manipulated for securing the actuator support in an appropriate position relative to the cover plate 46. Thus the device is readied for another cycle of operation.

In view of the foregoing, it should readily be apparent that the device of the instant invention provides a practical solution to the problem of accommodating testing of specimens in commercially available dewars, under practical loading conditions.

Although the invention has been herein shown and described in what is conceived to be the most practical and preferred embodiment, it is recognized that departures may be made therefrom within the scope of the invention, which is not to be limited to the illustrative details disclosed.

We claim:

1. In combination with a dewar, a device for tensioning test specimens disposed within a bath of cryogenic fluid confined within a chamber comprising:
    A. a support column adapted to be received within said chamber comprising a pair of plates including a bottom plate and a top plate and a plurality of compression members for supporting the plates in a mutually spaced relationship, each plate of said pair being of a disk-shaped configuration and characterized by an array of bores formed therein in coaxial alignment with the bores of the other plate of the pair;
    B. a plurality of anchor pins fixed within the array of bores characterizing the bottom plate, each pin of said plurality being adapted to receive a test specimen in an interconnected relationship therewith for thereby securing a plurality of test specimens to said support column;
    C. a plurality of axially displaceable pull rods extended into said chamber, each of said plurality being projected through a bore formed in the top plate of said support column and adapted to be connected at one end thereof to a test specimen rigidly secured to said support column, and characterized by a head formed at the opposite end thereof adapted to be received by a female connector;

D. a cover plate seated on said dewar for sealing the chamber and characterized by an array of bores through which sid plurality of pull rods are extended in an hermetically sealed relationship therewith;

E. a spacer of a cylindrical configuration interposed between said cover plate and said support column and connected thereto for securing said support column in place within said chamber;

F. an actuator support releasably mounted on said cover plate comprising a base plate and a top plate interconnected through a plurality of vertically oriented compression members;

G. an actuator including an axially retractable, vertically oriented shaft mounted on said actuator support;

H. a connecting link including a female coupling adapted to receive a head of a pull rod in a coupled relationship therewith; and I. a load cell connected to said link between said shaft and said pull rod for measuring tensile stress induced in the link.

* * * * *